(12) United States Patent
Shimuta

(10) Patent No.: US 12,109,051 B2
(45) Date of Patent: Oct. 8, 2024

(54) COVER

(71) Applicant: Murata Manufacturing Co., Ltd., Nagaokakyo (JP)

(72) Inventor: Toru Shimuta, Nagaokakyo (JP)

(73) Assignee: MURATA MANUFACTURING CO., LTD., Nagaokakyo (JP)

(*) Notice: Subject to any disclaimer, the term of this patent is extended or adjusted under 35 U.S.C. 154(b) by 752 days.

(21) Appl. No.: 17/318,178

(22) Filed: May 12, 2021

(65) Prior Publication Data
US 2021/0275270 A1 Sep. 9, 2021

Related U.S. Application Data

(63) Continuation of application No. PCT/JP2020/001431, filed on Jan. 17, 2020.

(30) Foreign Application Priority Data

Feb. 4, 2019 (JP) ................................. 2019-017730

(51) Int. Cl.
*A61B 50/30* (2016.01)
*A61B 5/00* (2006.01)
*A61B 5/0537* (2021.01)

(52) U.S. Cl.
CPC ............ *A61B 50/30* (2016.02); *A61B 5/0537* (2013.01); *A61B 5/4875* (2013.01); *A61B 5/682* (2013.01); *A61B 2050/3014* (2016.02); *A61B 2050/314* (2016.02)

(58) Field of Classification Search
CPC ...... A61B 2050/3014; A61B 2050/314; A61B 2562/0214; A61B 2562/247; A61B 5/053; A61B 5/0537; A61B 5/4277; A61B 5/4875; A61B 5/682; A61B 50/30; G01D 11/24
See application file for complete search history.

(56) References Cited

U.S. PATENT DOCUMENTS

| | | | | |
|---|---|---|---|---|
| 4,993,419 A | * | 2/1991 | Pompei | G01J 5/045 |
| | | | | 374/E1.013 |
| 2013/0150729 A1 | * | 6/2013 | Zuluage | A61B 5/0088 |
| | | | | 600/407 |

FOREIGN PATENT DOCUMENTS

| | | | | |
|---|---|---|---|---|
| EP | 1543768 A1 | * | 6/2005 | ............... A61B 5/00 |
| JP | 2008295472 A | | 12/2008 | |
| JP | 2018186880 A | | 11/2018 | |
| WO | 2004028359 A1 | | 4/2004 | |
| WO | 2014041585 A1 | | 3/2014 | |

OTHER PUBLICATIONS

Written Opinion of the International Search Authority issued for PCT/JP2020/001431, date of mailing Mar. 17, 2020.
International Search Report issued for PCT/JP2020/001431, date of mailing Mar. 17, 2020.

* cited by examiner

*Primary Examiner* — Eric J Messersmith
(74) *Attorney, Agent, or Firm* — ArentFox Schiff LLP

(57) ABSTRACT

A cover for use with a measuring device body that includes a sensor portion having a distal end with a sensor having a measurement surface and a proximal end opposite the distal end, and a grip connected to the proximal end of the sensor portion. The cover includes a cover member configured to cover the measurement surface of the sensor, and a support member at least on a side of the sensor portion opposite to the measurement surface, and the support member is connected to the cover member.

15 Claims, 5 Drawing Sheets

COVER

CROSS REFERENCE TO RELATED APPLICATIONS

The present application is a continuation of International application No. PCT/JP2020/001431, filed Jan. 17, 2020, which claims priority to Japanese Patent Application No. 2019-017730, filed Feb. 4, 2019, the entire contents of each of which are incorporated herein by reference.

FIELD OF THE INVENTION

The present disclosure relates to a cover to be used for a measuring device, such as an oral moisture measuring device.

BACKGROUND OF THE INVENTION

An oral moisture measuring device is a known example of a measuring device configured to be held by hand and to measure a measurement object (see Patent Document 1, for example). This oral moisture measuring device includes an electrical capacitance sensor that is brought into contact with a region to be measured and measures an amount of moisture of the measuring object (inside the oral cavity). In the oral moisture measuring device, a cover is normally fitted so as to cover the measurement surface of the sensor to prevent the measurement surface from coming into direct contact with the measuring object.

Patent Document 1: International Publication No. 2004/028359

SUMMARY OF THE INVENTION

The thickness of the cover that covers the measurement surface of the sensor as described above is normally thin so as not to affect the measurement sensitivity. The thin cover, however, is vulnerable to wrinkle generation at the measurement surface of the sensor depending on fitting conditions of the cover. Wrinkles affect measurement of the oral moisture measuring device.

A cover member that can suppress wrinkle generation is thus needed.

According to an aspect of the present disclosure, a cover is provided for use with a measuring device body that includes a sensor portion having a distal end with a sensor having a measurement surface and a proximal end opposite the distal end, and a grip connected to the proximal end of the sensor portion. The cover includes a cover member configured to cover the measurement surface of the sensor, and a support member at least on a side of the sensor portion opposite to the measurement surface, and the support member is connected to the cover member.

According to this configuration, the support member brings the cover member into contact with the measurement surface by pulling the cover member toward the side of the sensor portion opposite to the side having the measurement surface, which thereby suppresses generation of wrinkles of the cover member at the measurement surface.

According to the aspect of the present disclosure, a cover member that can suppress wrinkle generation can be obtained.

DETAILED DESCRIPTION OF THE PREFERRED EMBODIMENTS

Figure 1:
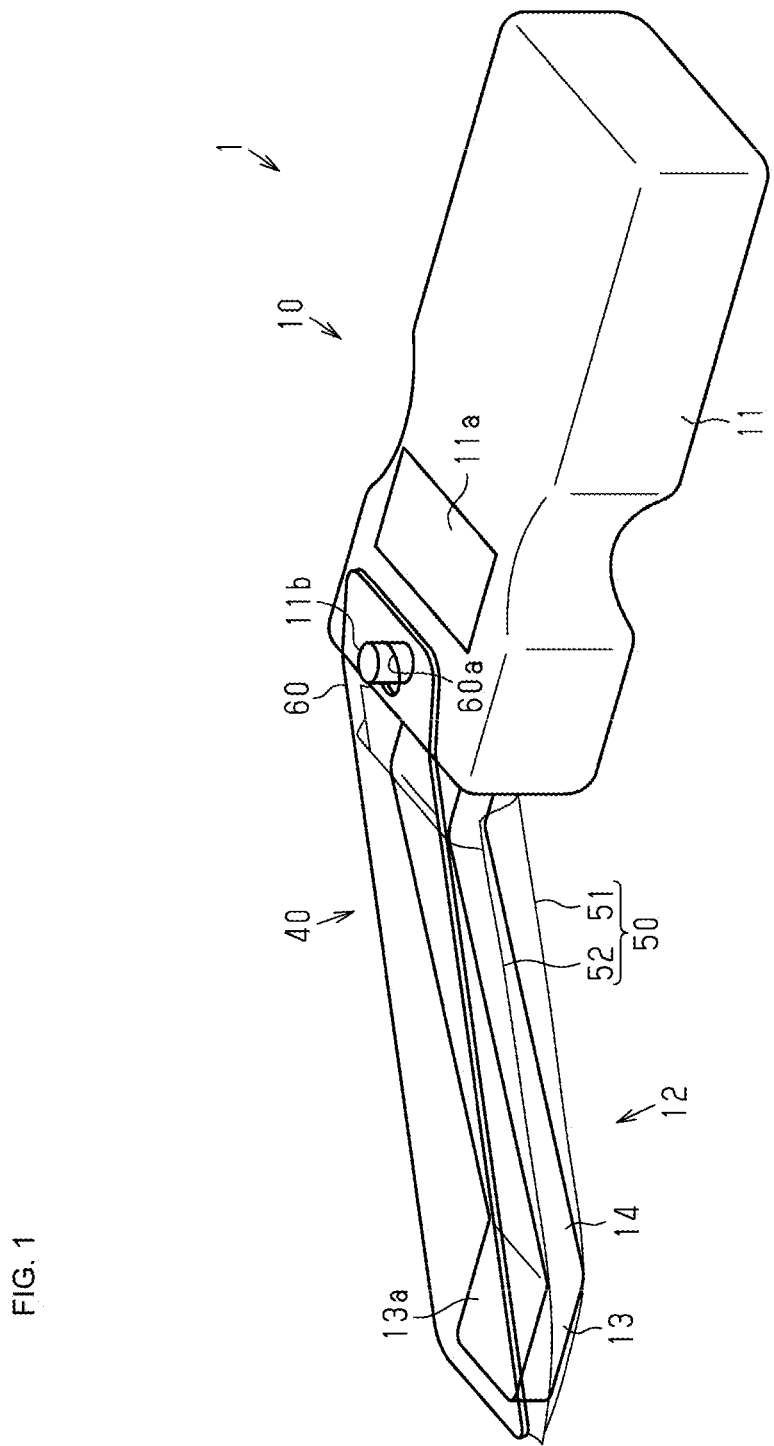
FIG. 1 is a perspective view illustrating an oral moisture measuring device.

A preferred embodiment will be described below.

Note that elements in the drawings may be illustrated in an exaggerated manner to facilitate better understanding. Dimensional relations of elements in the drawings may be different from those of the actual elements or may be different from each other.

As illustrated in FIG. 1, a measuring device 1 is, for example, an oral moisture measuring device for measuring the amount of intraoral moisture as the measurement object. The measuring device 1 includes a body 10 and a cover 40 to be attached to the body 10.

The body 10 includes a grip 11 disposed in an end region of the body 10 in the longitudinal direction and also includes a sensor portion 12 disposed in the other end region of the body 10. In the present embodiment, the sensor portion 12 extends in a direction opposite to the direction in which the grip 11 extends. The sensor portion 12 has a measuring portion 13 at a distal end thereof and a connection portion 14 that connects between the measuring portion 13 and the grip 11 at a proximal end thereof. A display 11*a* and a fixation portion 11*b* are formed on the grip 11.

Figure 2:
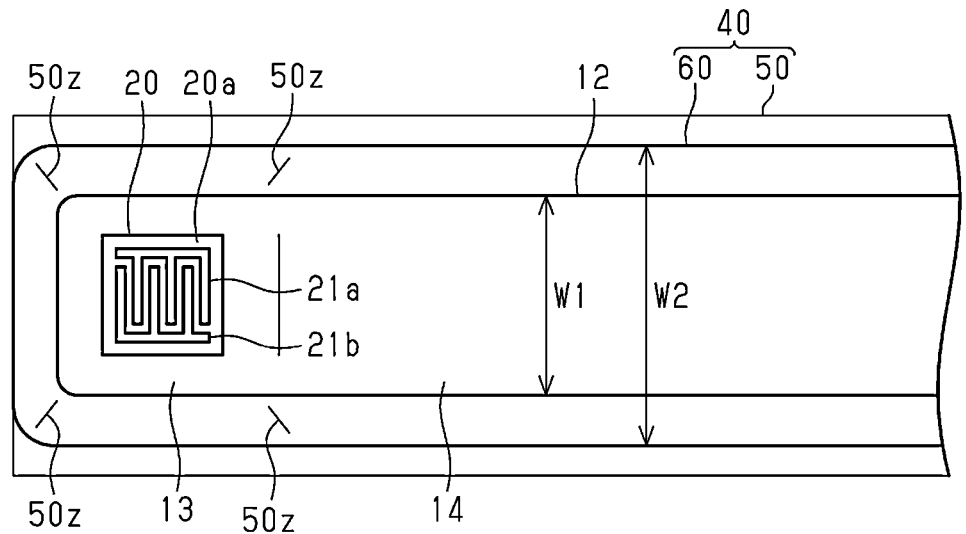
FIG. 2 is an enlarged view illustrating part of a sensor portion and of a cover.

As illustrated in FIG. 2, a sensor 20 is disposed in the measuring portion 13. The sensor 20 is shaped like a flat plate. The sensor 20 has a flat measurement surface 20*a*. For example, the sensor 20 is an electrical capacitance sensor. A pair of electrodes 21*a* and 21*b* are formed on the measurement surface 20*a* of the sensor 20. For example, the pair of electrodes 21*a* and 21*b* are disposed interdigitally.

The pair of electrodes 21*a* and 21*b* serve as electrodes of a capacitor. More specifically, the measurement surface 20*a* opposes a measurement object, and the measurement object and a liquid that covers the measurement object perform as dielectrics for the pair of electrodes 21*a* and 21*b*. The capacitance of the pair of electrodes 21*a* and 21*b* corresponds to the measurement object and the amount of water on the surface thereof.

The measuring device 1 includes a circuit board (not illustrated) on which components, such as an oscillation circuit and a control circuit, are mounted. The oscillation circuit outputs a signal with a frequency corresponding to the capacitance of the sensor. The control circuit detects the amount of water of the measurement object on the basis of the number of pulses of the output signal of the oscillation circuit. The control circuit displays the detected amount of water on the display 11*a*.

As illustrated in FIGS. 1 to 4, the cover 40 includes a cover member 50, a support member 60, and a connection member 70. In the present embodiment, the cover member 50 is a rectangular bag. The cover member 50 is preferably transparent or translucent. The cover 40 is attached to the body 10 such that the cover member 50 covers the measuring portion 13 positioned at the distal end of the sensor portion 12.

Figure 3:
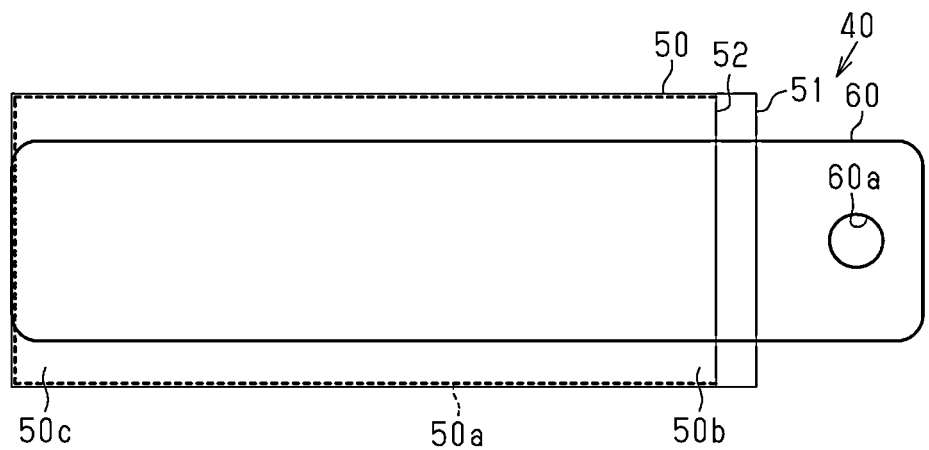
FIG. 3 is a schematic plan view illustrating the cover.

In the present embodiment, the cover member 50 is formed of a first cover sheet 51 and a second cover sheet 52 connected to the first cover sheet 51 at respective sides. Accordingly, the first cover sheet 51 and the second cover sheet 52 form a flat bag without gussets. For example, the first cover sheet 51 and the second cover sheet 52 may be welded to each other. In FIG. 3, the dotted line indicates the welded portion 50a. A side of the cover member 50 at which the first cover sheet 51 and the second cover sheet 52 are not welded is referred to as an opening end 50b, whereas the side of the cover member 50 opposite to the opening end 50b is referred to as a distal end 50c. Note that the cover member 50 may be formed into a bag by folding a single cover sheet into two leaves and connecting the leaves together. Alternatively, the cover member 50 may be formed using an adhesive, a double-sided adhesive tapes, or the like.

The material of the cover member 50 may be a resin having hydrophobic properties. The resin may be a thermoplastic resin. The resin having such properties is, for example, polyethylene (PE), polypropylene (PP), polyethylene terephthalate (PET), nylon, polyvinyl chloride, and polyimide.

The thickness of the cover member 50 is set so as to enable the sensor 20 to sense the measurement object (for example, the intraoral moisture) and so as not to disturb measurement. For example, the thickness of the cover member 50 may be 5 μm to 30 μm, and preferably 5 μm to 15 μm. The thickness of the cover member 50 may be adjusted appropriately in accordance with the material of the cover member 50. If the thickness of the cover member 50 exceeds 30 μm, the sensitivity of the sensor 20 drops considerably. The thickness can be measured using a contact-type instrument, such as a micrometer, or an optical-type instrument, such as an optical film thickness meter.

Figure 4:
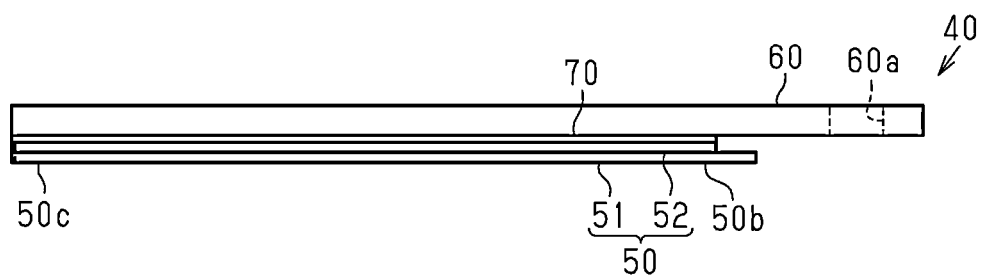
FIG. 4 is a schematic side view illustrating the cover.

As illustrated in FIG. 4, the connection member 70 connects between the support member 60 and the cover member 50. For example, the connection member 70 is an acrylic or silicon-based adhesive, a double-sided adhesive tape, or the like. The connection member 70 is preferably transparent or translucent.

In the present embodiment, the support member 60 is a rectangular plate. As illustrated in FIG. 2, the width W2 of the support member 60 is larger than the width W1 of the measuring portion 13. As illustrated in FIGS. 3 and 4, the support member 60 extends from the distal end 50c to the opening end 50b of the cover member 50. In addition, the support member 60 is longer than the cover member 50 and protrudes from the opening end 50b of the cover member 50. A through-hole 60a is formed in the support member 60 at a position outside the cover member 50. The through-hole 60a penetrates the support member 60 in the thickness direction. The through-hole 60a serves as an engagement portion for fixing the cover member 50 to the body 10. In other words, the through-hole 60a is used to fix the cover 40 to the grip 11 by connection to the fixation portion 11b. The support member 60 is preferably transparent or translucent.

The support member 60 is a rigid member. The material of the support member 60 may be higher in flexural modulus of elasticity and in flexural strength than that of the cover member 50. For example, the material of the support member 60 may be a resin, such as PET, ABS, polycarbonate, acrylic, and PP.

For example, the thickness of the support member 60 is 50 μm to 300 μm. Note that the thickness of the support member 60 may be set in accordance with the material to be used. For example, in the case of the material of the support member 60 being made of the same material as that of the cover member 50, the thickness of the support member 60 is preferably two or more to twenty or less times greater, more preferably five or more times greater, than the thickness of the cover member 50. Note that the thickness of the cover member 50 may be measured at the thickest portion or at the thinnest portion of the cover member 50. Alternatively, the thickness of the cover member 50 may be an average of thicknesses of the thickest portion and the thinnest portion of the cover member 50.

The cover 40 is attached to the grip 11 by inserting the fixation portion 11b of the grip 11 into the through-hole 60a of the support member 60. The cover 40 is detached from the body 10 by taking the support member 60 off the fixation portion 11b of the grip 11. In other words, the fixation portion 11b of the grip 11 and the through-hole 60a of the support member 60 enable the cover 40 to be attached to and detached from the grip 11.

Operation

In the present embodiment, the cover 40 can be attached to and detached from the grip 11 of the body 10.

When the cover 40 is attached to the body 10 with the cover member 50 covering the measurement surface 20a of the sensor 20, the support member 60 is positioned over a non-measurement surface 13a of the measuring portion 13, which is a surface opposite to the measurement surface 20a of the sensor 20. The support member 60 has a flexural modulus of elasticity greater than that of the cover member 50. Accordingly, the support member 60 pulls the cover member 50 toward the side of the measuring portion 13 having the non-measurement surface 13a. The tension force of the support member 60 acts substantially equally on the portions of the cover member 50 that cover the four sides of the quadrangularly shaped measuring portion 13, which thereby brings the cover member 50 into close contact with the measurement surface 20a of the sensor 20. Here, as illustrated in FIG. 2, wrinkles 50z are generated in the cover member 50 at positions outside the corners of the quadrangular measuring portion 13. Bringing the cover member 50 into close contact with the measurement surface 20a of the sensor 20 can suppress generation of wrinkles of the cover member 50 at the measurement surface 20a of the sensor 20.

In the present embodiment, the cover member 50 is a flat bag without gussets. The flat bag without gussets is beneficial in that the support member 60 can readily exert tension on the cover member 50. In addition, the flat bag without gussets can be manufactured easily by simply joining resin sheets together. Note that the cover member 50 may be formed into a bag having gussets.

During measurement, saliva adheres to the cover member 50, which may make it difficult to detach the thin cover member 50 from the measuring portion 13. In the present embodiment, however, the support member 60 extends from the distal end 50c to the opening end 50b of the cover member 50. Accordingly, the cover member 50 can be separated easily from the measuring portion 13 after measurement by using the support member 60, which makes it easier to remove the cover member 50 after measurement.

The through-hole 60a is formed through the support member 60, and the fixation portion 11b is formed on the grip 11. The cover 40 can be attached easily to the body 10 by engaging the through-hole 60a with the fixation portion 11b. The cover 40 can be detached from the body 10 easily by taking the through-hole 60a of the support member 60 off the fixation portion 11b of the grip 11.

The through-hole 60a for fixation is formed in the rigid support member 60. When the cover 40 is attached to the body 10, the support member 60 does not stretch but pulls the cover member 50 so as to brings the cover member 50 into contact with the measuring portion 13.

According to the above-described embodiment, the following advantageous effects can be obtained.

1) The measuring device 1 includes the body 10 and the cover 40 attached to the body 10. The body 10 has the sensor portion 12 having the measurement surface 20a of the sensor 20 at the distal end thereof and also has the grip 11 to which the sensor portion 12 is connected at the proximal end thereof. The cover 40 includes the cover member 50 made of a resin and configured to cover the measurement surface of the sensor 20 and also includes the support member 60 that is disposed at least on the side of the sensor portion 12 opposite to the side thereof on which the measurement surface 20a is disposed. The support member 60 is connected to the cover member 50. The support member 60 has a thickness greater than that of the cover member 50.

According to the cover 40, the support member 60 brings the cover member 50 into contact with the measurement surface 20a by pulling the cover member 50 toward the side of the sensor portion 12 opposite to the side having the measurement surface 20a, which can suppress generation of wrinkles of the cover member 50 at the measurement surface 20a.

2) The support member 60 extends from the distal end 50c of the cover member 50 to the opening end 50b thereof. Accordingly, the cover member 50 to which saliva is adhered after measurement can be separated easily from the measuring portion 13 by using the support member 60, which makes it easier to remove the cover member 50.

3) When the cover 40 is attached to the body 10, the rigid support member 60 through which the through-hole 60a for fixation is formed can pull the cover member 50 so as to brings the cover member 50 into contact with the measuring portion 13 without the support member 60 stretching.

Modification Examples

The above embodiment may be modified as described below.

The shapes of components in the above embodiment may be changed appropriately.

Figure 5:
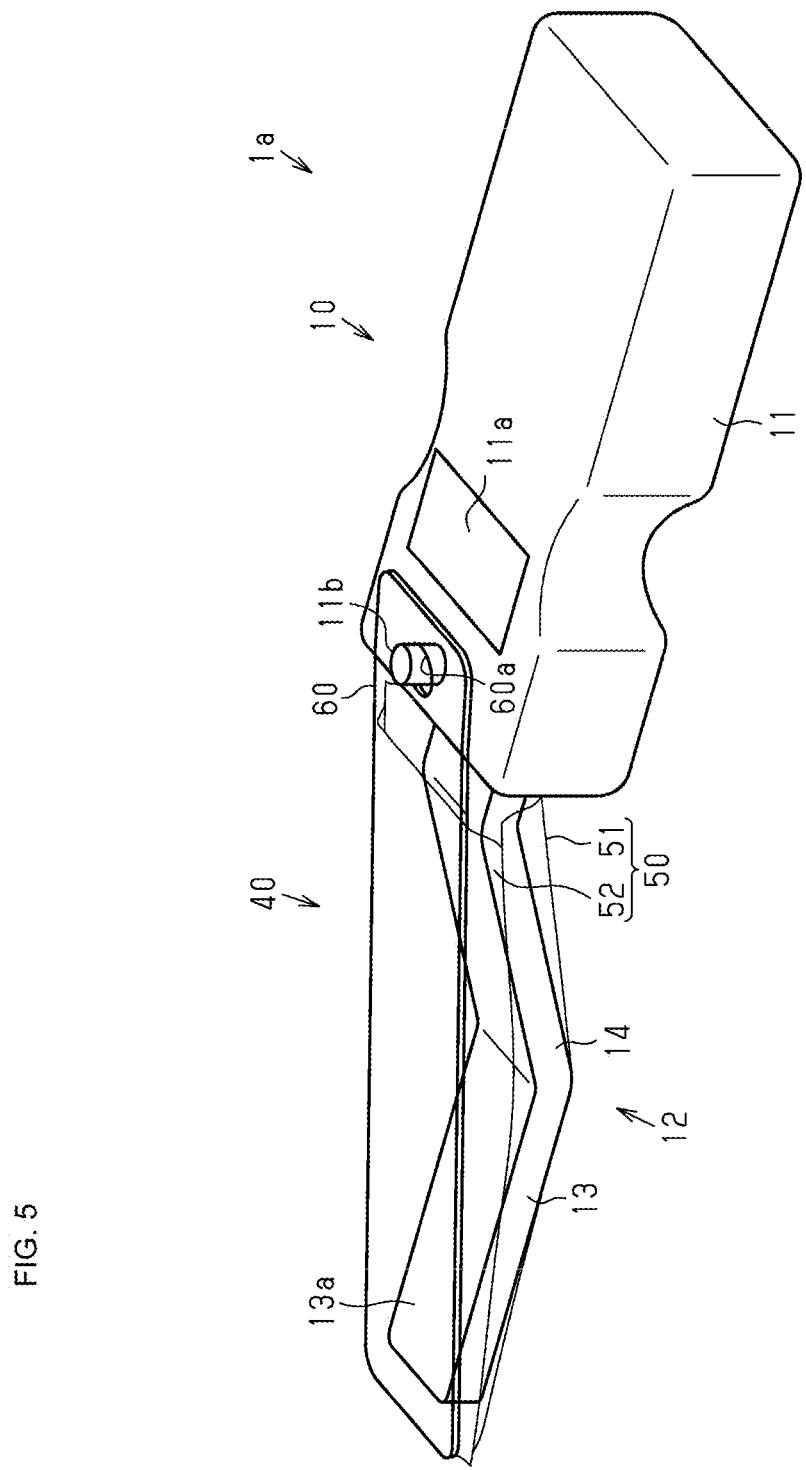
FIG. 5 is a perspective view illustrating a modification example of the oral moisture measuring device.

In a measuring device 1a illustrated in FIG. 5, the measuring portion 13 of the sensor portion 12 is shaped like an elongated rectangle. The measuring device 1a having such a measuring portion 13 is beneficial in that the distal end of the sensor 20 can be inserted into the oral cavity easily. Using this sensor portion 12 and the cover 40 as described in the above embodiment can suppress generation of wrinkles of the cover member 50 at the measurement surface 20a of the measuring portion 13.

In the above embodiment, the through-hole 60a is formed through the support member 60 of the cover 40, and the fixation portion 11b of the grip 11 is inserted in the through-hole 60a. The engagement between the support member 60 and the fixation portion 11b fixes the cover 40 to the grip 11. However, the structure for engagement between the support member 60 and the fixation portion 11b may be changed appropriately.

Figure 6A:
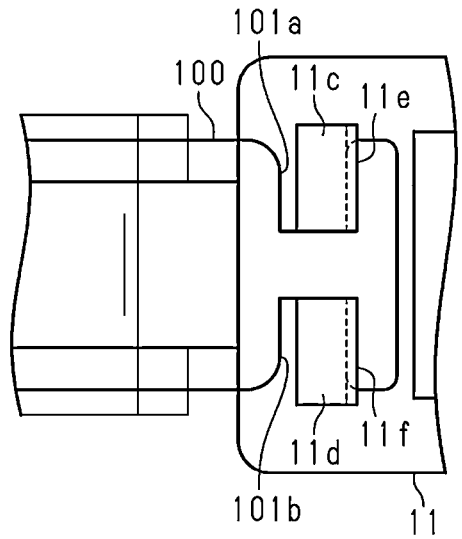
FIG. 6 (*a*) and FIG. 6 (*b*) are views illustrating a modification example of a support member and fixation portion.
Figure 6B:
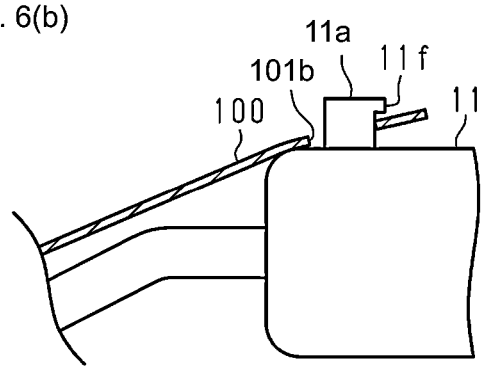

As illustrated in FIG. 6 (a), slits 101a and 101b serving as the engagement portion may be formed in a support member 100, and fixation portions 11c and 11d formed on the grip 11 engage respective slits 101a and 101b. The fixation portions 11c and 11d extend in a direction perpendicular to the direction from the grip 11 toward the distal end of the sensor portion 12. As illustrated in FIGS. 6 (a) and 6 (b), locking portions 11e and 11f are formed at respective upper ends of the fixation portions 11c and 11d so as to protrude in a direction opposite to the distal end of the sensor portion 12. The locking portions 11e and 11f prevent the support member 60 from coming off the fixation portion 11b. Note that the locking portions 11e and 11f having such a shape may be formed at the fixation portion 11b in the above-described embodiment.

In the above embodiment, the shape of the cover member 50 as viewed in plan may be changed appropriately.

Figure 7:
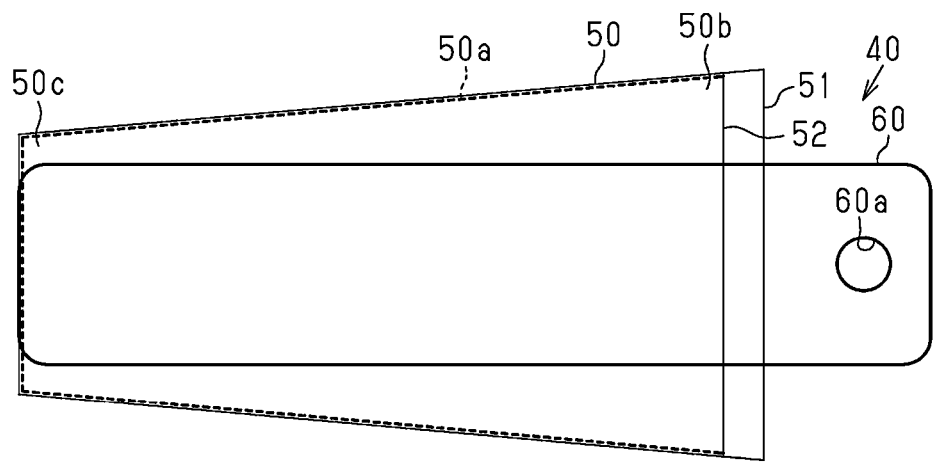
FIG. 7 is a schematic plan view illustrating a modification example of the cover.

As illustrated in FIG. 7, the cover member 50 may be shaped like a trapezoid in which the width of the cover member 50 gradually becomes large from the distal end 50c toward the opening end 50b. If the width of the distal end 50c of the cover member 50 is too large compared with the measuring portion 13 of the sensor portion 12, it may become more difficult to bring the cover member 50 into close contact with the measurement surface 20a of the sensor 20 even if the support member 60 pulls the cover member 50. As a result, wrinkles are more likely to be generated. In this modification example, however, the generation of the wrinkles can be suppressed since the size of the cover member 50 at the distal end 50c does not become too large relative to the measuring portion 13 of the sensor portion 12. In addition, the distal end 50c can be inserted into the oral cavity easily since the size of the cover member 50 at the distal end 50c does not become too large relative to the measuring portion 13 of the sensor portion 12. Moreover, the sensor portion 12 can be inserted into the cover member 50 easily since the cover member 50 has a width larger at the opening end 50b than at the distal end 50c.

The overall shape of the support member 60 of the above embodiment may be changed appropriately.

Figure 8:
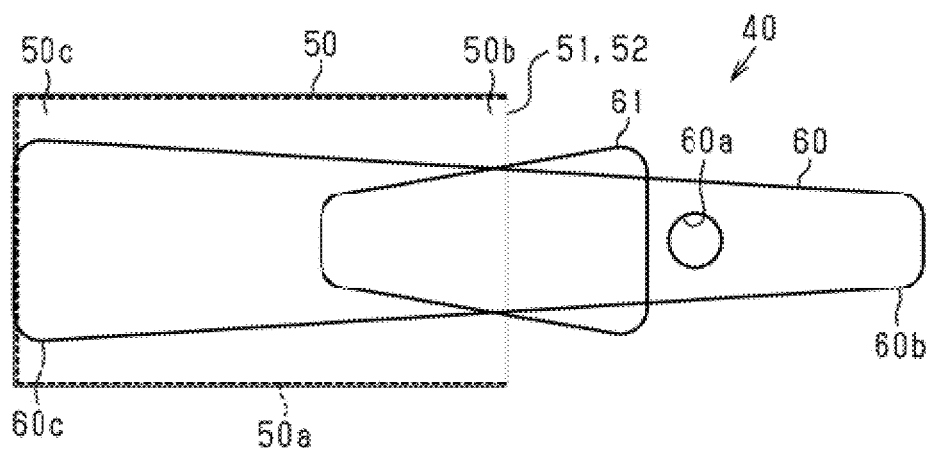
FIG. 8 is a schematic plan view illustrating a modification example of the cover.
Figure 9:
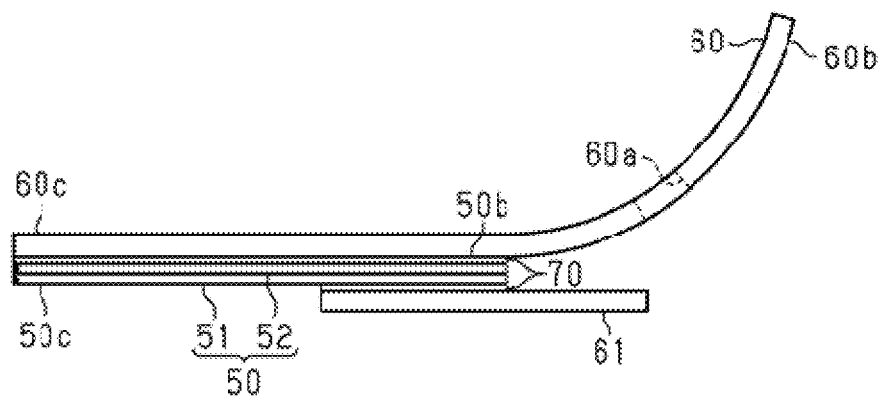
FIG. 9 is a schematic side view illustrating a modification example of the cover.

As illustrated in FIGS. 8 and 9, the support member 60 is shaped such that the width of the support member 60 gradually becomes small from an end portion 60c thereof near the distal end 50c of the cover member 50 toward an end portion 60b thereof near the opening end 50b of the cover member 50. The support member 60 has the smaller width near the opening end 50b of the cover member 50. This enables the opening of the cover member 50 to be shaped more flexibly so as to facilitate insertion of the sensor portion 12 into the cover member 50. Note that it is sufficient that the support member 60 has the smaller width portion near the opening end 50b of the cover member 50, and a portion of the support member 60 protruding from the opening end 50b of the cover member 50 may have a width that can be changed appropriately.

In addition, as illustrated in FIGS. 8 and 9, a retention member 61 may be connected to the first cover sheet 51. The retention member 61 is connected to the cover member 50 on a side of the cover member 50 opposite to the side having the support member 60. For example, the retention member 61 is connected to the first cover sheet 51 using the connection member 70, as is the case for the support member 60. The retention member 61 is connected to the first cover sheet 51 in such a manner that the retention member 61 does not overlap a portion of the first cover sheet 51 near the distal end of the cover member 50. In other words, the first cover sheet 51 is exposed near the distal end of the cover member 50. This enables the measurement surface 20a of the sensor 20 to be brought into contact with the measurement object with the first cover sheet 51 interposed therebetween. Accordingly, the thin first and second cover sheets 51 and 52 can be opened easily using the retention member 61 and the support member 60.

In the above embodiment, the bag-like cover may be formed by connecting the support member 60 illustrated in FIG. 4 to the first cover sheet 51. Alternatively, the bag-like cover may be formed by connecting the support member 60 to the second cover sheet 52.

In the above embodiment, the support member 60 illustrated in FIG. 4 may be formed by laminating multiple resin sheets. Moreover, at least one of the first cover sheet 51 and the second cover sheet 52 may be formed by laminating multiple resin sheets.

The configurations described in the above embodiment and modification examples may be replaced partially with known configurations appropriately. The embodiment and modification examples described above may be partially or entirely combined with one another.

REFERENCE SIGNS LIST 1 measuring device
10 body
11 grip
11b fixation portion
12 sensor portion
13 measuring portion
14 connection portion
20 sensor
20a measurement surface
40 cover
50 cover member
50b opening end
50c distal end
51 first cover sheet
52 second cover sheet
60 support member
60a through-hole
61 retention member

The invention claimed is:

1. A cover for use with a measuring device body that includes a sensor portion having a distal end with sensor having a measurement surface and a proximal end opposite the distal end, and a grip connected to the proximal end of the sensor portion, the cover comprising:
a cover member configured to cover the measurement surface of the sensor; and
a support member at least on a side of the sensor portion opposite to the measurement surface, the support member being connected to the cover member,
wherein the cover member has a distal end corresponding to the distal end of the sensor portion and an opening end opposite the distal end, and the support member extends from the distal end of the cover member to the opening end of the cover member.

2. The cover according to claim 1, wherein the support member has a thickness greater than that of the cover member.

3. The cover according to claim 1, wherein the support member is made of a same material as that of the cover member and the support member has a thickness two or more and twenty or less times greater than that of the cover member.

4. The cover according to claim 1, wherein the support member is made of a material having a flexural modulus of elasticity greater than that of a material of the cover member.

5. The cover according to claim 1, wherein
the cover member is a flat bag without gussets and has a first cover sheet and a second cover sheet that are connected to each other at respective edge portions, and
the support member is connected to the second cover sheet.

6. The cover according to claim 1, wherein the support member has a width that decreases from a first end portion of the support member near the distal end of the cover member toward a second end portion of the support member near the opening end of the cover member.

7. The cover according to claim 1, wherein the cover member has a width that increases from the distal end to the opening end thereof.

8. The cover according to claim 1, the cover further comprising:
a retention member disposed on a side of the cover member opposite to a side on which the support member is disposed such that the retention member does not overlap a distal end portion of the cover member.

9. The cover according to claim 1, wherein the cover member is a flat bag without gussets.

10. The cover according to claim 1, wherein the cover member is made of a resin material having hydrophobic properties.

11. A cover for use with a measuring device body that includes a sensor portion having a distal end with sensor having a measurement surface and a proximal end opposite the distal end, and a grip connected to the proximal end of the sensor portion, the cover comprising:
a cover member configured to cover the measurement surface of the sensor; and
a support member at least on a side of the sensor portion opposite to the measurement surface, the support member being connected to the cover member, wherein
the grip includes a fixation portion,
the support member has a protruding portion that protrudes past the opening end of the cover member, and
the protruding portion has an engagement portion configured to engage the fixation portion of the grip.

12. The cover according to claim 11, wherein the engagement portion is a through-hole.

13. The cover according to claim 11, wherein the engagement portion is one or more slits, and the fixation portion includes corresponding locking portions to the one or more slits that protrude in a direction opposite to the distal end of the sensor portion.

14. The cover according to claim 11, wherein the support member has a width that decreases from a first end portion of the support member near the distal end of the cover member toward a second end portion of the support member near the opening end of the cover member.

15. A cover for use with a measuring device body that includes a sensor portion having a distal end with sensor having a measurement surface and a proximal end opposite the distal end, and a grip connected to the proximal end of the sensor portion, the cover comprising:
a cover member configured to cover the measurement surface of the sensor; and
a support member at least on a side of the sensor portion opposite to the measurement surface, the support member being connected to the cover member, wherein
the cover member has a width that increases from the distal end to the opening end thereof.

* * * * *